(12) United States Patent
Eder

(10) Patent No.: US 8,771,311 B2
(45) Date of Patent: Jul. 8, 2014

(54) SURGICAL INSTRUMENT AND METHOD FOR IMPROVING A CRESTAL SINUS LIFT

(75) Inventor: Klaus Eder, Perchtoldsdorf (AT)

(73) Assignee: JEDER GmbH, Vienna (AT)

( * ) Notice: Subject to any disclaimer, the term of this patent is extended or adjusted under 35 U.S.C. 154(b) by 752 days.

(21) Appl. No.: 11/953,436

(22) Filed: Dec. 10, 2007

(65) Prior Publication Data

US 2008/0319466 A1    Dec. 25, 2008

(30) Foreign Application Priority Data

Dec. 11, 2006    (AT) .............................. A 2044/2006

(51) Int. Cl.
*A61M 29/00*    (2006.01)
(52) U.S. Cl.
USPC .......................................... 606/199; 606/196
(58) Field of Classification Search
CPC ................... A61C 8/0092; A61B 2017/00106
USPC ......... 600/433–435, 437–439, 466–470, 585; 606/162, 167, 196, 199
See application file for complete search history.

(56) References Cited

U.S. PATENT DOCUMENTS

| | | | |
|---|---|---|---|
| 2004/0084049 A1* | 5/2004 | Baran | 128/207.14 |
| 2006/0149306 A1* | 7/2006 | Hart et al. | 606/191 |
| 2008/0132889 A1* | 6/2008 | Wakamatsu et al. | 606/41 |
| 2008/0200916 A1* | 8/2008 | Murphy | 606/94 |

FOREIGN PATENT DOCUMENTS

| | | |
|---|---|---|
| DE | 103 22 869 B3 | 1/2004 |
| DE | 103 59 304 A1 | 7/2005 |
| EP | 1 174 094 A1 | 1/2002 |
| EP | 1 269 933 A2 | 1/2003 |
| EP | 1 362 561 A2 | 11/2003 |
| WO | WO/2006/044073 | 4/2006 |
| WO | WO 2006/096900 | 9/2006 |

\* cited by examiner

*Primary Examiner* — Sameh Boles
(74) *Attorney, Agent, or Firm* — Henry M. Feiereisen LLC

(57) ABSTRACT

A surgical instrument for use in a sinus lift includes a substantially cylindrical sleeve which is sealingly insertable into a bore of a jawbone. The sleeve has a lumen and is formed with an inlet channel and an outlet port which is in fluid communication with the lumen. A vibration unit is operatively connected to the instrument for transmitting vibrations into the lumen.

17 Claims, 2 Drawing Sheets

SURGICAL INSTRUMENT AND METHOD FOR IMPROVING A CRESTAL SINUS LIFT

CROSS-REFERENCES TO RELATED APPLICATIONS

This application claims the priority of Austrian Patent Application, Serial No. A 2044/2006, filed Dec. 11, 2006, pursuant to 35 U.S.C. 119(a)-(d), the content of which is incorporated herein by reference in its entirety as if fully set forth herein.

BACKGROUND OF THE INVENTION

The present invention relates to a surgical instrument for performing a sinus lift in particular a crestal sinus lift.

Nothing in the following discussion of the state of the art is to be construed as an admission of prior art.

Sinus lift involves a surgical procedure in which the membrane of the maxillary sinus is partly detached and lifted from the jawbone to provide a space between bone and maxillary sinus membrane. Inserted into the provided space is an autologous bone, e.g. from the Tuber maxillae, the Linea oblique, the chin region, or from the iliac crest (bone replacement materials, bone chip) or a synthetic bone replacement material, e.g. bone replacement material, commercially available by Geistlich AG under the trade name Bio-Oss, oftentimes blended with autologous bone. This material is intended to transform into bone within 6 months to ensure a solid foundation for an implant.

The conventional procedure for a sinus lift requires preparation of a mucoperiosteal flap in the buccal molar region and to cut an oval window in the thus exposed bone, without damage to the subjacent maxillary sinus membrane. The oval-shaped bone disk hanging from the maxillary sinus membrane is then gently pressed in a direction of the maxillary sinus, while the membrane is separated from the bone around the window with the aid of special instruments. As the maxillary sinus membrane is very delicate, comparable to an egg skin, this procedure is being executed very carefully because of the risk to damage the maxillary sinus membrane. The space provided in this manner in the maxillary sinus is then filled with bone replacement material through the window and the buccal window is covered with a film. The film is normally made of absorbable material, e.g. a membrane which is commercially available by Geistlich AG under the trademark Bio-Gide. Subsequently, the mucoperiosteal flap is sealingly sutured. The procedure is very invasive and subjects the patient to great stress as a result of substantial swelling and discoloration of up to 10 days, and possibly of pain.

This surgical procedure is oftentimes referred to as "open" or "classic" sinus lift. If sufficient residual bone height is available, approximately at a height of 5 mm, implants can be inserted simultaneously with the sinus lift (single-stage sinus lift). The implants can be fully strained only after the bone replacement material has hardened. When the residual bone height is too low, the implants are inserted in a second surgery about 6-8 months following the sinus lift (two-stage sinus lift).

The so-called crestal sinus lift is oftentimes carried out without folding of a bone plate. The access to the maxillary sinus is made possible from the maxillary crest. The mucous membrane of the mouth is hereby opened from the toothless part of the maxillary crest up to the bone and the bone is scraped by a cylindrical cutter in the shape of a tunnel up to slightly underneath the maxillary sinus membrane. A cylindrical instrument is then carefully tapped in a direction of the maxillary sinus so that a thin bone disk is pressed in the direction of the maxillary sinus, whereby the maxillary sinus membrane adheres upon the top of bone disk. The maxillary sinus membrane is hereby lifted in the form of a tent and tensed. As the bore is too small (diameter of about 4 mm), there is no possibility to separate the maxillary sinus membrane with instruments from the bone around the bore. After the maxillary sinus membrane has been elevated, bone replacement material is introduced via the bore. The surgery may also be performed in two separate stages or simultaneously. This minimally invasive procedure is however limited to cases which require only slight buildup of bone height for insertion of the implant.

Another instrument allows realization of a greater cavity during the crestal sinus lift and involves a balloon which is introduced through the bore to the pointed end of the instrument and gently inflated so that the maxillary sinus membrane separates from the bone. As the force is applied only at the tip of the balloon upon the maxillary sinus membrane, it is not possible to evenly distribute the tension so that a premature rupture (bursting) of the maxillary sinus membrane can occur.

Published European Patent Appl. No. EP 1 362 561 A1 describes an apparatus for preparation of a sinus bottom elevation. A pump is connected to a fluid source and conveys a controlled volume of fluid for injection into the maxillary sinus. The sinus membrane is hereby elevated by the jet of fluid flowing through the access port and separated from the jawbone. A sensor measures pressure values in the flow path of the fluid. A perforation of the maxillary sinus membrane can be deduced from changes in the pressure values. Even when this jet is only gentle in nature, the use of a fluid jet causes pressure peaks at those sites where the jet impacts the sinus membrane. Elevation of the sinus membrane is possible only through the application of the fluid jet because of the underpressure in the interior as a result of a sealing of the outer bore end by means of suction cups. Thus, it is not possible to build up excess pressure in the cavity to be expanded, without the suction cup losing effectiveness and falling off.

German Pat. No. DE 103 22 869 B3 describes a device for carrying out a sinus bottom elevation, using a treatment instrument for creating an access or an insertion channel in the jaw being treated. The device has a pulsating pressure medium source connected to the treatment instrument which is provided with at least one pressure medium feed and a pressure medium outlet over its length. Separation of the sinus membrane is hereby effected by a pulsating flushing by which an absorbable membrane inserted through the bore should be unfolded, like an umbrella, between sinus membrane and inlet port. This procedure is required because, on one hand, there is hardly any possibility to control the internal pressure as a result of the drainage, and, on the other hand, the direct impact of a flushing pulse upon the sinus membrane may easily cause injury thereof. This known device has also other shortcomings. Firstly, any damage to the sinus membrane will remain essentially unrecognized during lifting of the sinus membrane. Secondly, the unfolding of the absorbable membrane and thus the assumption of a correct disposition cannot be monitored or influenced. Thirdly, the internal pressure increases and the sinus membrane ruptures, when the drainage of fluid from the maxillary sinus membrane is clogged.

International Publ. No. WO 2006/044073 describes an apparatus for installing a dental implant in the alveolar ridge and including a sleeve which is inserted through the alveolar ridge to the maxillary sinus. A source of flowing material is positioned at the lower end of the sleeve and injects flowing material through the sleeve into a cavity between the ridge and the subantral membrane to thereby increase bone mass. This apparatus has the drawback that the sinus membrane is separated from the bone solely by the effect of the hydrostatic pressure. As soon as a point is reached when the sinus membrane no longer can separate from the bone, pressure needs to be increased, quickly reaching the stress limit of the sinus membrane.

FIGS. 1 and 2 show schematically a conventional method for performing a sinus lift. A laterally prepared bone plate 17 is hereby pressed into the maxillary sinus and folded upwardly like a flap to detach the maxillary sinus membrane 7 from the bone and to thereby form a body cavity 6 beneath the bone plate 17. Special instruments can be inserted through a comparably large bone window 20 to separate the maxillary sinus membrane 7 from the jawbone 8. Bone replacement material is then filled through the window 20 into the body cavity 6, while the bone plate 7 remains in the cavity. The bone window 20 is then closed by an absorbable film and the initially detached mucoperiosteal flap is securely stitched over it.

It would therefore be desirable and advantageous to provide an improved surgical instrument to obviate prior art shortcomings.

SUMMARY OF THE INVENTION

According to one aspect of the present invention, a surgical instrument for use in a sinus lift includes a substantially cylindrical sleeve which is sealingly insertable into a bore of a jawbone, with the sleeve having a lumen and formed with an inlet channel and an outlet port in fluid communication with the lumen, and a vibration unit operatively connected to the sleeve for transmitting vibrations into the lumen.

When performing a crestal sinus lift, the sleeve of the surgical instrument according to the present invention is inserted into a bore in the crest of the jawbone to establish a fluid communication to the body cavity which is intended to be expanded between the jawbone and the maxillary sinus membrane. Working fluid is introduced via an inlet channel with the aid of a simple syringe under slight pressure to slightly expand the body cavity. The vibration unit causes the fluid, which is under slight pressure, to vibrate.

The present invention resolves prior art problems by effecting the detachment of the sinus membrane not only by the applied pressure but primarily by the pulsating vibration introduced by the vibration unit upon the fluid. Changes in pressure, caused by the vibration unit, are negligible and cannot cause rupture of the sinus membrane. Pressure and vibrations occur evenly in the entire body cavity so that stress peaks which could cause damage to the maxillary sinus membrane are prevented. When the sinus membrane separates by a further piece from the bone, the pressure of the fluid decreases as a greater space is made available between the sinus membrane and the bone wall. Pressure is thus predominantly employed to lift the sinus membrane and to fill the interstices. The separation of the sinus membrane from the bone is caused by the pulsations. As a result, detachment of the sinus membrane is effected at slight pressure of the fluid in a gentle and reliable manner so that the risk of rupture is minimal.

The vibration unit may be implemented as an ultrasonic transducer which is permanently or detachably secured to the surgical instrument. The ultrasonic transducer is able to cause high frequency pulsations of the fluid that is introduced under slight pressure into the body cavity so that the maxillary sinus membrane can be separated from the bone in an especially gentle manner. Introduction of additional fluid allows further expansion of the body cavity.

According to another feature of the present invention, a flange may be attached to the sleeve to limit a penetration depth of the sleeve into the bore of the jawbone. The flange may hereby be movably attached to the sleeve for securement of the flange at different heights. By limiting the penetration depth to different depths, damage to the maxillary sinus membrane by the free end of the sleeve can be avoided. In addition, the penetration depth of the sleeve can be adjusted such that the free sleeve end extends beyond the bone inner wall by about 1 to 2 mm, when the instrument is inserted into the bore of the jawbone. As a result, the bone disk, which after providing the bore remains in the jawbone anteriorly of the instrument and separates the bore from the maxillary sinus, can be pushed with the instrument, e.g. through slight tapping, in the direction of the maxillary sinus without the need for a separate instrument.

According to another feature of the present invention, a sealing element may be attached to the sleeve, e.g. latex hose which is placed over the sleeve. By sealingly closing the bore, pressure in the interior of the body cavity can be precisely controlled from outside. The sealing may be realized in a form-fitting manner. The use of a latex hose, however, is simple and easy to replace. Of course, other sealing elements, such as a sealing ring, may also be attached to the sleeve.

When the instrument and the vibration unit are detachably connected, the detachable connection may be realized by contact points on the instrument for the vibration unit. As a result, the use of an external ultrasonic transducer is also possible in an easy and reliable manner. An external ultrasonic transducer may be a commercially available device and can be secured to the respective contact point or pressed against it, with the pulsations being introduced into the fluid via the instrument.

According to another feature of the present invention, the vibration unit may be received within the instrument and in communication with the lumen. In this way, the need to handle a separate external ultrasonic transducer is eliminated and the user is able to focus on other manipulations, such as pressure control, without being restricted by handling the ultrasonic transducer.

According to another feature of the present invention, the instrument may have a handle for manipulating the surgical instrument and may include a pressure control device for limiting a pressure buildup in the lumen. In this way, the instrument is easy to handle and can be safely operated.

According to another aspect of the present invention, a system includes a surgical instrument having a substantially cylindrical sleeve which is sealingly insertable into a bore of a jawbone, with the sleeve having a lumen and formed with an inlet channel and an outlet port in fluid communication with the lumen; a vibration unit operatively connected to the sleeve for transmitting vibrations into the lumen, a feed conduit fluidly connected to the lumen, a reservoir fluidly connected to the feed conduit for storing and making available a fluid so that a fluid communication is established between the reservoir and the outlet port of the sleeve for feeding fluid to a body cavity, and a pressure-application unit acting on the fluid for building and controlling a working pressure in the fluid, with the pressure-application unit being constructed for varying the pressure of the fluid.

According to another feature of the present invention, a pressure gauge may be provided for measuring the pressure of the fluid, e.g. a physiological saline solution. The use of a physiological saline solution is beneficial and generally available in clinics.

This system allows easy handling of the surgical instrument and enhances operating safety because the pressure of the fluid can be constantly monitored and controlled during surgery. Pressure is constantly held to a desired level by the pressure-application unit, on one hand, and a rapid pressure buildup can quickly be recognized and countermeasures such as reducing the pressure can be quickly taken to prevent rupture of the sinus membrane.

According to another feature of the present invention, an automatic switch-off device may be operatively connected to the pressure gauge for limiting the pressure of the fluid to a maximum value. Measurement and control of pressure not only enhances operating safety but also allows recognition of a pressure buildup, indicating a maximally possible expansion of the body cavity.

According to yet another aspect of the present invention, a method of elevating the membrane from an inner wall of the maxillary sinus includes the steps of opening an access to the maxillary sinus, injecting a fluid under pressure via the access to the maxillary sinus to thereby lift the membrane from the inner wall of the maxillary sinus, and introducing a bone replacement material into a space between the membrane and the inner wall of the maxillary sinus via the access to the maxillary sinus.

According to another feature of the present invention, the access may be established from the maxillary crest.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
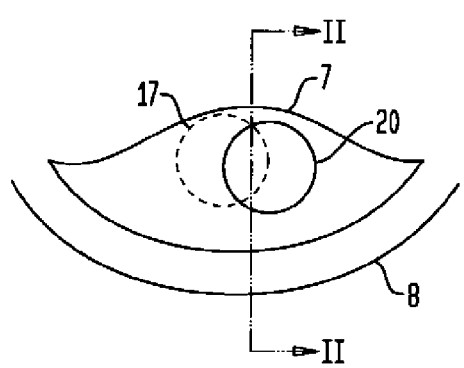
FIG. 1 is a schematic illustration of a conventional sinus lift.
Figure 2:
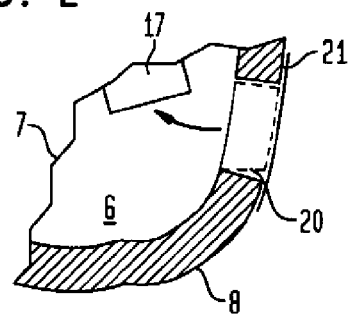
FIG. 2 is a section view taken along the line II-II in FIG. 1.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Figure 3:
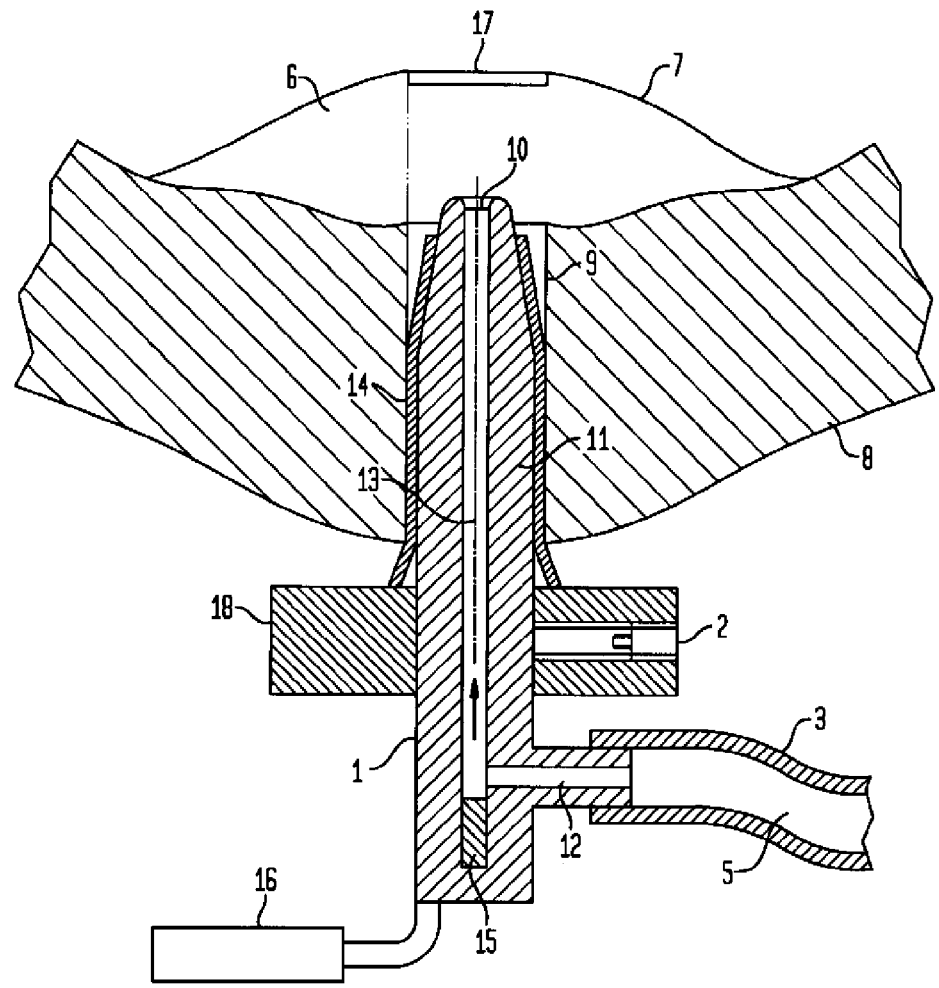
FIG. 3 is a section view of a surgical instrument according to the present invention.

Turning now to the drawing, and in particular to FIG. 3, there is shown a section view of a surgical instrument 1 according to the present invention. The surgical instrument 1 includes a sleeve 11 which is inserted in a bore 9 of the jawbone 8. The bore 9 can be made, for example, with the aid of a cylindrical cutter in the jawbone 8. The bore is not drilled all the way through so that a thin bone plate 17 remains at the end of the bore 9. Before insertion of the sleeve 11 of the instrument 1, a flange 18 is placed over a sleeve 11 and secured in place at a distance to the sleeve tip in dependence on the bone thickness. The flange 18 may be secured in place by a screw fastener 2 which is received in the flange 18 and provided with an internal socket so that the screw fastener 2 does not extend out from the side and constitute an obstacle. By tightening the screw fastener 2, the end thereof is pressed against the sleeve 11 to prevent further shift of the flange 18.

The forward length of the sleeve 11 is adjusted in such a manner that the sleeve 11 can be pushed into the bore 9 far enough for the sleeve tip to penetrate the maxillary sinus by 1 to 2 mm. Before being inserted, a seal 14 is placed over the sleeve 11, e.g. an open-topped latex hose, as shown in FIG. 3. Apart from the sealing action, the seal 14 provides a secure hold of the instrument 1 in the bore 9 and dampens transmission of pulsations onto the bone.

When the instrument 1 is inserted in the bore 9, the tip of the sleeve 11 pushes the retained bone plate 17 into the maxillary sinus by only 1 to 2 mm because otherwise there is a risk of damage to the maxillary sinus membrane 7. The bone plate 17 is hereby separated from the bone 8 while still adhering to the maxillary sinus membrane 7. The sleeve 11 may have different diameters depending on the application at hand. When a crestal sinus lift is involved, the spatial conditions are mostly limited in view of the width of the maxillary crest. The bore 9 should have a diameter to allow insertion of an implant in a single surgery. On the other hand, the bore 9 should be wide enough to enable introduction of bone replacement material through the bore 9 into the body cavity. Normally, tooth implants require a bore 9 with a diameter of about 4 mm, which is sufficient for introduction of bone replacement material. Suitably, the surgical instrument 1 is made of rust-resistant and foodstuff-compatible steel and has a central lumen 13 via which working fluid can be fed from an inlet channel 12 into the body cavity 6. At its lower end, the instrument 1 has a handle 16 by which the instrument 1 can be manipulated and extracted from the bore 9 again.

The sleeve 11 is rounded at its distal outlet port 10. The rear area of the sleeve 11 has a cylindrical configuration which then tapers toward the front to facilitate insertion into the bore 9. When the sleeve 11 has a diameter of 4 mm, the leading sleeve portion may taper along a length of 6 mm to a diameter of 3 mm at the sleeve tip.

When the instrument 1 is inserted into the bore 9, fluid, e.g. physiological saline solution (NaCl) is injected through the central lumen 13 under gentle pressure. This may be realized by a syringe. However, in order to enable precise pressure control, the provision of an automatic pressure control and monitoring device is currently preferred, as will be described in greater detail with reference to FIG. 4.

The saline solution under pressure causes the maxillary sinus membrane 7 to be slightly elevated from the bore 9 so that the saline solution is able to fill the body cavity 6 between the jawbone 8 and the maxillary sinus membrane 7. As the fluid is only under slight pressure when introduced into the instrument 1, this pressure is normally not sufficient by itself to separate the maxillary sinus membrane 7 far enough from the bone in an area about the bore 9. Therefore, in addition to the applied pressure, a vibration unit 15, e.g. an ultrasonic transducer, is provided to transmit high-frequency pulsations onto the fluid. The pulsation may be transmitted to the fluid by simply pressing an external ultrasonic transducer against the instrument 1. Currently preferred is, however, the placement of an ultrasonic transducer 15 in the bottom of the sleeve 11. Another option is the provision of a vibratory pump by which the fluid can be caused to vibrate.

As the pressure is evenly distributed in the fluid, the presence of pressure peaks is eliminated and thus the risk of premature rupture is prevented. The pulsations, suitably in the ultrasonic range, introduce into the fluid energy which primarily acts at the boundary between maxillary sinus membrane 7 and jawbone 8 so that the sinus membrane gently separates from the bone. When a sufficient volume has been introduced so that the body cavity 6 has a sufficient size, the instrument 1 is extracted from the bore 9. As the body cavity 6 is still filled with fluid, the patient is asked to exert pressure, like in sneezing, while holding the patient's nose, causing excess pressure in the maxillary sinus by which the fluid is drained through the bone tunnel into the cavity of the mouth. Subsequently, viscous bone replacement material (e.g. Bio-Oss), possibly blended with body-inherent bone meal, can be injected through the bone tunnel into the created space. When a single-stage (simultaneous) surgery is possible, an implant is inserted immediately following which closes the bone tunnel and extends to the body cavity 6 where it is surrounded by the bone replacement material. After about 6 months, the bone replacement material has substantially transformed into bone so that it can be exposed to stress and establishes also a firm connection with the implant which, in turn, can then be exposed to stress.

When a classic sinus lift is involved, the bore 9 is closed, after being filled with bone replacement material, with a membrane, and the opening is tightly stitched shut. The implant (or implants) is (are) inserted only after the bone replacement material has hardened.

Figure 4:
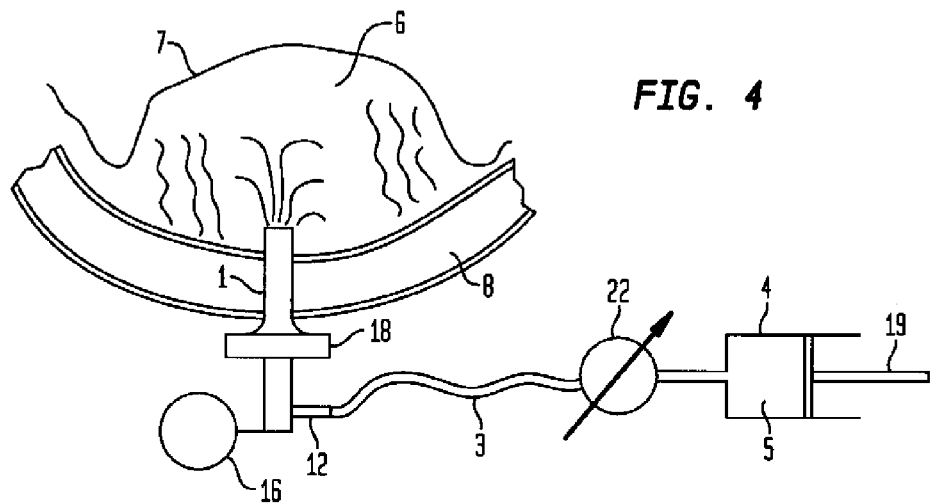
FIG. 4 is a schematic illustration of an overall system employing the surgical instrument of FIG. 3.

Referring now to FIG. 4, there is shown a schematic illustration of an overall system employing the surgical instrument 1 of FIG. 3. A hose 3 connects the instrument 1 via a pressure gauge 22 to a reservoir 4 in which working fluid 5 is under pressure with the aid of a pressure-application unit 19. The reservoir 4 and the pressure-application unit 19 are shown in FIG. 4 as piston pump. Of course, any other type of apparatus which effect a controllable pressure of the fluid 5 is conceivable as well. The pressure in the fluid 5 is measured by the pressure gauge 22 which is operatively connected to an automatic switch-off device to limit the pressure in the fluid 5 to a maximum level.

Figure 5:
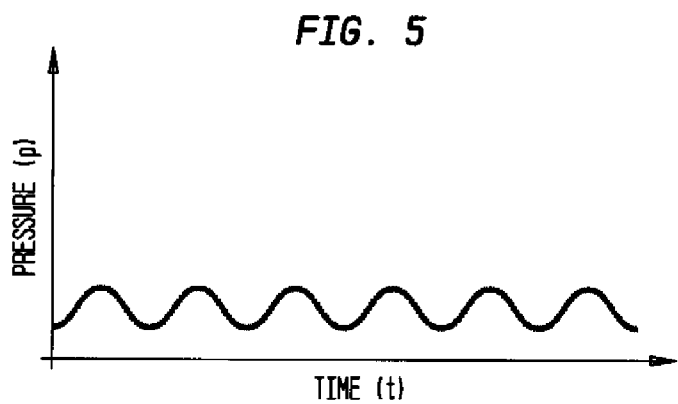
FIG. 5 is a graphical illustration of a pressure profile of the fluid during expansion of the body cavity.

The pressure applied by the pressure-application unit 19 causes the supply of fluid 5 to expand the body cavity 6. The required separation of the maxillary sinus membrane 7 from the jawbone 8 is hereby effected by the working pressure only to a limited extent but rather is effected by the introduced (ultrasonic) waves. A typical pressure profile is hereby established during "pumping up" of the body cavity 6, as shown in FIG. 5. In FIG. 5, the pressure profile is plotted with the pressure as a function of time, and a wavy pattern is formed which can be explained by the slight drop in pressure when a further piece of the maxillary sinus membrane 7 has separated from the bone and a greater volume is available for the fluid 5 in the body cavity 6. As the volume is filled by added fluid, the pressure increases again until a further piece of the maxillary sinus membrane 7 has separated from the bone and the pressure drops again. As a result, the pressure profile is waved, while overall progressing horizontal.

Figure 6:
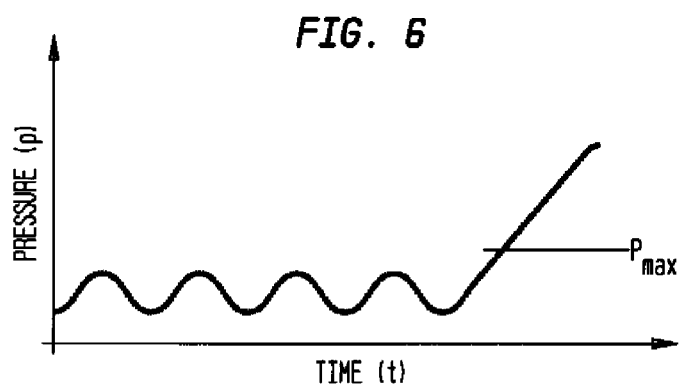
FIG. 6 is a graphical illustration of a pressure profile of the fluid when the body cavity reaches maximum expansion.

This pressure profile remains as long as the maxillary sinus membrane 7 is able to separate from the bone. Once, there is no longer any separation of the maxillary sinus membrane 7, despite an increase in pressure, the pressure curve ascends quickly, as shown in FIG. 6 at the end of the pressure profile. The increase in pressure is an indication that the maxillary sinus membrane 7 is close to rupture (burst). As the pressure is limited by the switch-off device to a maximum value $p_{max}$, the possibility of rupture can be prevented as the pressure-application unit 19 is spontaneously turned off.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

What is claimed is:

1. A surgical instrument for detaching a sinus membrane from a jawbone during a sinus lift, comprising:
   a substantially cylindrical sleeve having a dull distal tip, said sleeve sealingly insertable into a predrilled bore of the jawbone, said sleeve having a not more than one lumen, the not more than one lumen extending entirely along the sleeve from a proximal end of the sleeve to the distal tip of the sleeve, said not more than one lumen containing a fluid under pressure; and
   a vibration unit operatively connected to the sleeve to cause vibrations of the fluid in the lumen and transmission of the vibrations to an area outside the lumen to promote in the area outside of the lumen an elevation of the sinus membrane from the jawbone.

2. The surgical instrument of claim 1, for use in a crestal sinus lift.

3. The surgical instrument of claim 1, wherein the lumen has an inlet channel which is in fluid communication with a feed conduit for the fluid.

4. The surgical instrument of claim 1, wherein the vibration unit has an ultrasonic transducer.

5. The surgical instrument of claim 4, wherein the ultrasonic transducer is detachably fixed to the sleeve.

6. The surgical instrument of claim 5, wherein the sleeve has contact points for effecting a detachable connection of the ultrasonic transducer to the sleeve.

7. The surgical instrument of claim 4, wherein the ultrasonic transducer is permanently fixed to the sleeve.

8. The surgical instrument of claim 1, further comprising a flange attached to the sleeve to limit a penetration depth of the sleeve into the bore of the jawbone.

9. The surgical instrument of claim 8, wherein the flange is movably attached to the sleeve for securement of the flange at different heights.

10. The surgical instrument of claim 1, further comprising a sealing element attached to the sleeve.

11. The surgical instrument of claim 10, wherein the sealing element is a latex hose placed over the sleeve.

12. The surgical instrument of claim 1, wherein the vibration unit is received within the sleeve and operatively connected with the lumen.

13. The surgical instrument of claim 1, further comprising a handle connected to the sleeve for manipulating the surgical instrument.

14. The surgical instrument of claim 1, further comprising a pressure control device for limiting a pressure buildup in the lumen.

15. The surgical instrument of claim 1, wherein the fluid is a physiological saline solution.

16. The surgical instrument of claim 1, further comprising a pressure application unit for introducing the fluid into the sleeve at a pressure sufficient to elevate the sinus membrane from the jawbone in conjunction with the vibrations generated by the vibration unit.

17. The surgical instrument of claim 16, wherein the pressure-application unit is a syringe.

* * * * *